United States Patent
Ottleben

(10) Patent No.: US 8,673,199 B2
(45) Date of Patent: Mar. 18, 2014

(54) METHOD FOR PRODUCING AN ORTHESIS

(75) Inventor: Michael Ottleben, Kalefeld (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 474 days.

(21) Appl. No.: 12/525,370

(22) PCT Filed: Jan. 31, 2008

(86) PCT No.: PCT/DE2008/000192
§ 371 (c)(1),
(2), (4) Date: Mar. 15, 2010

(87) PCT Pub. No.: WO2008/092443
PCT Pub. Date: Aug. 7, 2008

(65) Prior Publication Data
US 2011/0232837 A9    Sep. 29, 2011

(30) Foreign Application Priority Data

Jan. 31, 2007 (DE) .......... 10 2007 005 733
Aug. 28, 2007 (DE) .......... 10 2007 040 467

(51) Int. Cl.
*B29C 70/36* (2006.01)
(52) U.S. Cl.
USPC .......................................... 264/257; 602/23
(58) Field of Classification Search
USPC ............. 264/257; 602/23, 5, 6, 7, 8; 156/242, 156/246
See application file for complete search history.

(56) References Cited

U.S. PATENT DOCUMENTS

| | | | |
|---|---|---|---|
| 3,329,143 A | | 7/1967 | Gordon |
| 4,289,122 A | | 9/1981 | Mason et al. |
| 4,572,167 A | * | 2/1986 | Brunswick ................ 602/19 |
| 4,672,955 A | * | 6/1987 | Cooper ........................ 602/5 |
| 5,362,304 A | * | 11/1994 | Varn ........................... 602/19 |
| 5,520,529 A | * | 5/1996 | Heckel ...................... 425/218 |
| 5,540,652 A | * | 7/1996 | Callinan et al. ............ 602/1 |
| 5,573,501 A | | 11/1996 | Ruscito |
| 6,991,610 B2 | * | 1/2006 | Matsumoto et al. ........ 602/4 |
| 7,367,074 B1 | * | 5/2008 | Bergquist ................. 12/142 N |
| 2002/0123709 A1 | | 9/2002 | Goble et al. |
| 2004/0077979 A1 | * | 4/2004 | Karason et al. ............ 602/3 |
| 2004/0176714 A1 | | 9/2004 | Darcey |

FOREIGN PATENT DOCUMENTS

| | | |
|---|---|---|
| DE | 19506912 | 9/1995 |
| DE | 69732541 | 2/2006 |
| EP | 1317912 | 6/2003 |
| EP | 1114626 | 2/2005 |
| WO | WO86/07533 | 5/1986 |
| WO | WO 2004037425 | 5/2004 |

\* cited by examiner

*Primary Examiner* — Galen Hauth
(74) *Attorney, Agent, or Firm* — Whitham, Curtis, Christofferson & Cook, P.C.

(57) ABSTRACT

The invention relates to an orthesis (2) comprising at least one plate-shaped part which is adapted to a body part (3). A deformable plate-shaped support (4) is provided with a curable material (5, 9) and, after adapting the shape of the support (4) by direct deformation onto the body part (3), the curable material (5, 9) present on the support (4) is cured in the shape of the support. The invention allows adaption of the orthesis to the body part (3) without production of a template.

9 Claims, 1 Drawing Sheet

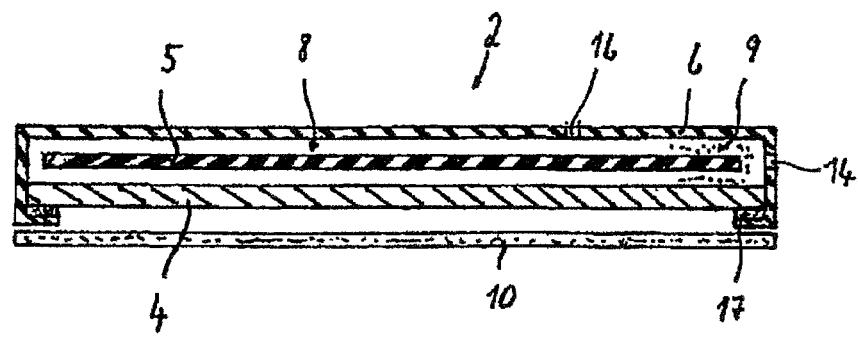
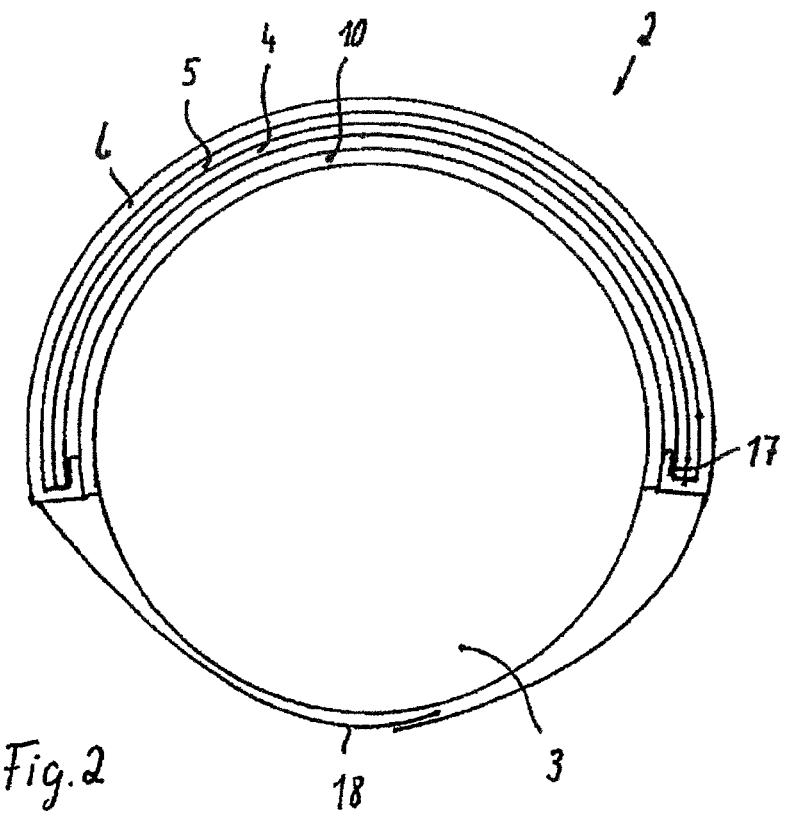

METHOD FOR PRODUCING AN ORTHESIS

FIELD OF THE INVENTION

The invention relates to a method for producing an orthosis with at least one plate-shaped part which is adapted to a body part.

BACKGROUND

Orthoses are used to support and hold body parts whose function is impaired by disease or accident. The orthosis bears with at least one plate-shaped part on the body part. Particularly in the case of orthoses that are to be worn permanently or over a long period of time, it is important that the plate-shaped part is well adapted to the body part.

DE 195 06 912 C2 discloses a method for producing a knee-joint orthosis composed of an upper leg part and a lower leg part that are connected to each other by means of joints and that can be produced individually according to a plaster cast. A plate made of thermoplastic and assigned to the upper leg, and another assigned to the lower leg, are cut to a shape defined by the model produced according to a plaster cast. The cut plates are heated to a predetermined temperature that permits deformation. The heated and cut plates are shaped on the produced model and secured by bandages. In this way, an upper leg part and a lower leg part are formed. Joint adapters are fitted to the model, and the joints are secured thereon. Thermoplastic linkage arms provided on the joints are heated and fixed by bandages. Bridge elements in the form of connecting strips of thermoplastic are shaped on the upper leg part and lower leg part in such a way that they extend between the ends of the linkage arms. After cooling, the bandages are removed, and the individual parts of the complete orthosis structure are bonded together by a plastic adhesive. This method is complicated and requires that a model, on which the orthosis is then secured, be produced by means of a plaster cast.

SUMMARY

The object of the present invention is to make available a method that simplifies the adaptation of the plate-shaped parts to the body part.

In a method according to the invention, this object is achieved by the fact that a deformable plate-shaped support is provided with a curable material and, after the shape of the support has been adapted by deformation directly on the body part, the curable material present on the support is cured in the shape of the support.

The method according to the invention is therefore based on the concept that the curable material is deformed along with the deformable plate-shaped support by deformation of the plate-shaped support directly on the body part, and the plate-shaped support retains the shape by virtue of its dimensional stability, such that the curable material is cured in the shape of the deformed support, namely the support adapted to the shape of the body part.

The plate-shaped support can, during curing, remain in the orthosis as part thereof or can be removed from the curable material after the latter has been cured. For removal, it is obviously necessary that the curable material has no form-fit connection to the plate-shaped support, which can also be formed by a lattice material. For this purpose, it may be expedient to incorporate a separating means or a separating film between the support and the curable material.

The curable material can be applied on the side of the plate-shaped support directed away from the body part, on the side directed toward the body part or on both sides. This applies in particular when the curable material used is in the form of carbon fibers pre-impregnated by means of resin, a plastic-coated fiber composite material or a thermoplastic fiber composite material. The use of carbon fibers pre-impregnated with resin is preferred, preferably in the form of known prepreg tissue layers with which a laminate layer of predetermined thickness can be obtained by arrangement in a stack comprising a suitable number of layers. The resin used can be a thermoplastic or a thermosetting plastic. Whereas the thermosetting plastic is in practice no longer deformable after crosslinking, in particular by heat, the use of a thermoplastic permits remodeling of the plate-shaped part of the orthosis by local application of heat, as can be achieved in a known manner by warm air, ultrasound, high frequency, infrared radiation, etc.

In another embodiment, the curable material contains a fiber material enclosed by a film or a tube, and a casting resin is introduced into the space enclosed by the tube or the film. After the plate-shaped support has been shaped, the casting resin is then cured with the fiber material as laminate. The curing can be by a chemical reaction, by application of heat, etc. In these cases, it is therefore expedient if a heat-insulating material is applied on the side of the plate-shaped support directed toward the body part. In this case, the curing can take place directly after the deformation of the plate-shaped support on the body part itself. Preferably, the heat-insulating material can be removed again after the curable material has been cured. A pad can then be applied in its place, which improves the wearing comfort of the orthosis.

The introduction of the casting resin into the space enclosed by the film or the tube can be made easier by generating an underpressure in the space. In this way, an inclusion of air bubbles can in particular be avoided. Alternatively, the film or the tube can be pressed onto the laminated plate before the casting resin is cured.

The fiber material can be in the form of loose, woven or knitted fibers or fibers connected to form a nonwoven, in particular of carbon, glass, polyamide, Kevlar and other plastics.

A heat-shrinkable tube can preferably be used as the tube.

If the orthosis needs a joint, the latter is preferably fixed by an external frame and then connected to the produced plate-shaped parts.

The plate-shaped support according to the invention must be able to deform easily on the body part, but must retain the adopted shape, such that the curable material, in particular the fiber-reinforced material, adopts the shape of the plate-shaped support and retains this shape during curing. The plate-shaped support can be formed by a thin plate of light metal, for example aluminum. It is also possible to use a lattice structure, which is preferably made of metal.

The plate-shaped support can also be formed from at least two layers with mutually facing surface topographies which, for example under vacuum, are pressed onto each other and, after deformation, hook onto each other with their surface profiles and thus retain the shape adapted to the body part. Suitable surface topographies are ribbed profiles, but also irregular profiles, for example of the kind found on coarse abrasive paper.

The plate-shaped support can also be in the form of bandages that are made deformable by a binder with dimensional stability. The laminating material can in this case be placed onto the body part, if appropriate with a pad therebetween, and pressed against the body by means of the bandage, such that the shape of the body part is adopted by the laminating material. The bandages can then be fixed with their binder, which binder can be a hardening plastic or a drying plaster. The laminating material can then be cured in the shape fixed by the bandages, so as to adapt to the shape of the body part.

DESCRIPTION OF THE DRAWINGS

An embodiment of an orthosis produced according to the invention is shown schematically in the attached drawing, in which:

FIG. 1 shows a schematic structure of the layers of an orthosis according to the invention, and FIG. 2 shows a section through a body part, for example a thigh, with the orthosis according to FIG. 1 applied.

DETAILED DESCRIPTION

In the figures of the drawing, identical and corresponding structural parts are designated by the same reference signs.

The drawing shows a schematic depiction of an orthosis 2 which, with a plate-shaped part, can be adapted in terms of size and shape to a body part 3, for example a thigh.

The orthosis 2 comprises a plate-shaped support 4, here in the form of a thin plate of aluminum, onto whose side directed away from the body part a material or substance, for example carbon fibers or the like, is laminated. For this purpose, fiber material 5, for example a carbon fiber layer, is draped onto the plate and impregnated with a resin, for example epoxy resin. To do so, the plate 4, with the fiber material 5 applied thereon, is first of all tightly covered by a tube or a film 6 whose edge engages under the plate 4 and is connected to the plate 4, for example bonded to it by means of an adhesive 17. Casting resin 9 is then introduced, for example injected by means of a syringe, into the space 8 enclosed by the film 6 and impregnates the fiber material 5. The plate 4 treated in this way is then adapted to the body part 3 in order to shape the orthosis. Thereafter, the casting resin 9 is cured and adopts the shape of the deformed plate 4.

The lamination and the introduction of the casting resin can take place before the orthosis has been applied and adapted in shape.

The lamination with casting resin and carbon fibers can also take place directly onto the body part 3, in which case, however, after the material 5 to be laminated has been applied on the side of the plate 4 directed away from the body part or on both sides of the plate 4, a heat-insulating material is first applied on the side of the plate 4 directed toward the body part or on both sides of the plate 4, in order to avoid a situation where heat resulting from a chemical reaction, during curing of the casting resin, acts on the skin of the body part 3.

Thereafter, as in the first-described method, the prepared plate 4 is covered by a film 6, and casting resin 9 is then introduced into the space 8 enclosed by the film 6. Thereafter, the plate 4 which has been prepared thus far and is still malleable is adapted to the body part 3 to form the orthosis. Thereafter, the casting resin 9 cures, and a pad 10 is applied on the side of the orthosis directed toward the body part, with the heat-insulating material preferably being removed beforehand.

After the material to be laminated, i.e. fiber material 5, has been applied on the side of the plate 4 directed away from the body part, and after the plate 4 thus treated has been covered by the film 6, it is also possible to first of all apply a pad 10 to the side of the plate 4 directed toward the body part and then to adapt the plate 4, thus far prepared, to the body part 3 so as to form the orthosis. Thereafter, the orthosis 2 shaped on the body part 3 is removed, and casting resin 9 for saturating the fiber material is introduced into the space 8 enclosed by the film 6 and is cured.

By pressing the film 6 onto the laminated plate 4 before the casting resin 9 is cured, air can be removed from the space B, in order in this way to produce a uniform laminate. This is achieved even more effectively if an underpressure is generated in the space 8 filled with the casting resin 9, by means of which underpressure the composite made up of film 6, laminate and plate 4 is pressed together, as a result of which any air and excess resin that may be present is drawn off before the casting resin 9 is cured. This underpressure can be generated by a pump, which is attached to a suitable opening 14 (indicated by broken lines in FIG. 1) of the film envelope 6. Air and excess casting resin 9 can then flow off upward through a second opening 16 (indicated by broken lines in FIG. 1) arranged at the top part. Instead of the above-described film 6 and the pump for generating an underpressure, a heat-shrinkable tube can also be used.

The pressure can alternatively be generated with the aid of elastic magnetic plates (not shown).

In the presence of a joint, for example a knee joint, the latter is fixed by an external frame (not shown).

For particularly secure orthoses, it is recommended to incorporate a core (not shown) into the middle of the material 5 to be laminated, and this core can also be chosen such that it is able to take over the function of the plate 4 by virtue of slight and dimensionally stable deformability.

The pad 10 can be applied to the side of the orthosis 2 directed toward the body part either before or after the casting resin is cured.

Instead of the fiber material 5, which is saturated by the casting resin 9, a fiber material pre-impregnated with a resin, for example epoxy resin, can also be used, for example a carbon fiber layer 5 pre-impregnated with resin or epoxy resin. This eliminates the step of introducing casting resin 9 into the space 8 enclosed by the film 6. If a pre-impregnated fiber material is used, the film 6 is also no longer required.

The material 5 to be laminated can also be applied on the side of the plate 4 directed toward the body part or on both sides of the plates 4. The laminating with the material pre-impregnated with resin, or the carbon fiber layer pre-impregnated with resin, can take place directly on the body part 3.

FIG. 2 shows a schematic section through a body part 3, for example a thigh, with an orthosis 2 according to the invention in the form of a plate-shaped shell, composed of an aluminum shell 4 which is laminated on the outside or on both sides by means of carbon fibers 5 and whose inner face (side directed toward the body part) is provided with a padding material 10 and is covered by a resilient film 6, the edge of which engages under the aluminum shell 4 and is connected to the aluminum shell 4, for example bonded to it (adhesive 17). The space 8 enclosed by the film 6 contains casting resin 9 which, in the cured state, provides the dimensional stability of the orthosis 2. The orthosis 2 can be mounted on the body part 3, for example the thigh, by means of a closure element 18, for example a velcro-type closure.

The use of carbon fibers 5 pre-impregnated with resin has the effect that the orthosis 2, which is otherwise of the same design, differs in terms of the fact that a film 6 is no longer required.

As material to be laminated, or instead of material pre-impregnated with resin, it is also possible to use plastic-coated fiber composite material or thermoplastic fiber composite material. The curing preferably takes place by applying heat.

The invention claimed is:

1. A method for producing an orthosis with at least one plate-shaped part which is adapted to a thigh, comprising:
   providing a deformable metal plate-shaped support with a solidifiable material connected to said metal plate-shaped support, wherein said solidifiable material comprises a fiber material enclosed by a film or a tube;
   removing air enclosed by said film or said tube to produce a uniform laminate;
   deforming said support on a thigh to produce an adapted shape fitted to said thigh, whereby said metal plate-shaped support retains said adapted shape by virtue of dimensional stability of said metal plate-shaped support;
   removing said metal plate-shaped support and said solidifiable material from said thigh;
   heating said solidifiable material present on said metal plate-shaped support in the adapted shape of said metal plate-shaped support, said heating step producing a solidified part in said adapted shape; and
   removing said metal plate-shaped support from the solidified part in said adapted shape.

2. The method as claimed in claim 1, wherein the solidifiable material is a carbon fiber layer pre-impregnated with resin.

3. The method as claimed in claim 1, wherein a heat-insulating material is applied on a side of said metal plate-shaped support which will be directed toward said thigh, and further comprising the step of removing said heat-insulating material together with said metal plate-shaped support after producing a solidified part in said adapted shape in said heating step.

4. The method as claimed in claim 1, wherein said tube or said film is heat-shrinkable.

5. The method as claimed in claim 1, wherein the metal late-shaped support comprises a joint, further comprising a step of connecting said joint to said solidified part using an external frame.

6. The method as claimed in claim 3, further comprising a step of replacing said heat-insulating material and said metal plate-shaped support on a side of said solidifiable material with a pad after producing said solidified part.

7. A method for producing an orthosis which is adapted to a body part, comprising the steps of:
   providing a metal plate-shaped support;
   covering one surface of the metal plate-shaped support with a fiber material;
   tightly encasing the fiber material and plate-shaped support with a film or tube;
   introducing a casting resin between the plate-shaped support and the film or tube to impregnate the fiber material;
   deforming the metal plate-shaped support on a body part to produce an adapted shape fitted to said body part, whereby the metal plate-shaped support retains the adapted shape by virtue of dimensional stability of said metal plate-shaped support;
   removing the metal plate-shaped support from the body part after deformation;
   removing air from a space enclosed by the film or tube to produce a uniform laminate;
   curing the casting resin to adopt the shape of the deformed metal plate-shaped support to produce a solidified part; and
   removing said metal plate-shaped support from the solidified part in said adapted shape, which solidified part forms part of an orthosis which is adapted to the body part.

8. A method for producing an orthosis which is adapted to a body part, comprising the steps of:
   providing a metal plate-shaped support;
   draping a fiber material onto one surface of the metal plate-shaped support;
   tightly covering the fiber material and said metal plate-shaped support with a film whose edges engage under the metal plate-shaped support and are connected to the metal plate-shaped support by means of an adhesive;
   impregnating the fiber material with a casting resin by introducing the casting resin into a space enclosed by the film to impregnate the fiber material;
   deforming the metal plate-shaped support on a body part to produce an adapted shape fitted to said body part, whereby the metal plate-shaped support retains the adapted shape by virtue of dimensional stability of said metal plate-shaped support;
   removing the metal plate-shaped support from the body part after deformation;
   removing air from a space enclosed by the film to produce a uniform laminate;
   curing the casting resin to adopt the shape of the deformed metal plate-shaped support to produced a solidified part; and
   removing said metal plate-shaped support from the solidified part in said adapted shape, which solidified part forms part of an orthosis which is adapted to the body part.

9. The method as claimed in claim 8, wherein a heat-insulating material is applied on a side of said metal plate-shaped support which will be directed toward said body part, and further comprising the step of removing said heat-insulating material after producing a solidified part in said adapted shape in the curing step.

* * * * *